United States Patent [19]

Freti et al.

[11] Patent Number: 4,842,674
[45] Date of Patent: Jun. 27, 1989

[54] METHOD OF MEASUREMENT OF THE RATE OF OXIDATION OF A METAL MELT

[75] Inventors: Silvano Freti, Chippis; Kurt Buxmann, Sierre, both of Switzerland

[73] Assignee: Swiss Aluminium Ltd., Chippis, Switzerland

[21] Appl. No.: 490,125

[22] Filed: Apr. 29, 1983

[30] Foreign Application Priority Data

May 19, 1982 [CH] Switzerland ............ 3126/82

[51] Int. Cl.$^4$ ............................................. G01J 5/20
[52] U.S. Cl. ................................. 156/601; 250/338.1; 250/338.3; 250/338.5; 374/139
[58] Field of Search .......... 75/60; 156/601, DIG. 61, 156/DIG. 74, DIG. 76; 250/338, 338.1, 338.3, 338.5; 374/120, 139, 129

[56] References Cited

U.S. PATENT DOCUMENTS

| | | | |
|---|---|---|---|
| 3,493,770 | 2/1970 | Dessauer et al. | 156/601 X |
| 4,177,094 | 12/1979 | Kroon | 148/175 |
| 4,421,554 | 12/1983 | Mahn et al. | 75/60 X |

OTHER PUBLICATIONS

System for the Measurement of Spectral Emittance at High Temperature; Hyton et al.; AIAA Journal; vol. 14, No. 9, Sep. '76, 1303-1310.
Heteroepitaxial Semiconductors for Electronic Devices; Cullen et al.; Springer-Verlag, N.Y.; 1978 pp. 182-189.

Primary Examiner—Barry S. Richman
Assistant Examiner—Timothy M. McMahon
Attorney, Agent, or Firm—Bachman & LaPointe

[57] ABSTRACT

A process for measuring the rate of oxidation on the surface of a metal melt wherein the oxide skin on the melt surface is removed at constant temperature and the electromagnetic radiation during the subsequent oxidation is measured with an infra-red radiation pyrometer such that the variation in intensity of the electromagnetic radiation indicates the rate of oxidation. The process can also be employed for measuring the concentration in a metal melt of the elements influencing the rate of oxidation.

2 Claims, 2 Drawing Sheets a b

METHOD OF MEASUREMENT OF THE RATE OF OXIDATION OF A METAL MELT

BACKGROUND OF THE INVENTION

The present invention relates to a method of measuring the rate of oxidation on the surface of a metal melt, especially a melt of aluminum or of an aluminum alloy.

The oxidation behavior of metal melts can be strongly influenced by dissolved metallic elements, which can be present as impurities and/or alloying components. For example, the presence of lithium or magnesium in an aluminum melt leads to an increase in the rate of oxidation.

In foundries, the oxidation of metal melts is made apparent by the formation of dross. Dross formation can become a significant cost factor as a consequence of the loss of metal which occurs. Therefore, efforts are being made to reduce the quantity of dross to a minimum. The formation of dross is decisively influenced by the rate of oxidation of the metal melt, that is, the speed with which an oxide skin forms.

The measurement of the rate of oxidation of a metal melt is usually carried out as follows: the oxide skin is removed from the melt surface at different intervals of time and, after dissolving out the metallic components, is filtered, roasted, weighed out and analyzed.

In light of the foregoing it would be highly desirable to provide a method for measuring the rate of oxidation at the surface of a metal melt and also determine the concentration in the metal melt of the elements influencing the rate of oxidation in a simple manner.

SUMMARY OF THE INVENTION

According to the present invention, the foregoing object is achieved wherein the oxide skin on the melt surface is removed at constant temperature, and the electromagnetic radiation during the subsequent oxidation is measured with an infra-red radiation pyrometer such that the variation in intensity of the electromagnetic radiation is taken as a measure of the rate of oxidation, or of the concentration of the oxidation influencing elements.

By the removal of the oxide skin, an oxide-free metal surface is created for a short time. By the oxidation which at once sets in again, a new oxide skin is formed, while at the same time the emission behavior of the metal surface varies, and with it the intensity of the thermal radiation emanating from it. The decline in intensity of the electromagnetic radiation as a function of time thereby reflects at least qualitatively the rate of oxidation at the metal surface. Quantitative results can be obtained with the help of standardizing measurements. In the same way, the concentrations of the elements contained in the metal melt which influence the rate of oxidation can be determined.

The method according to the invention is in particular suited for investigations into the short-term oxidation behavior of melt surfaces of aluminum and aluminum alloys, and indeed also of other metals such as for example copper or steel. The method has proved to be particularly advantageous in the determination of the lithium content in aluminum melts.

BRIEF DESCRIPTION OF THE DRAWINGS

Further advantages, features and details of the present invention will appear from the following description and with reference to the drawings wherein.

DETAILED DESCRIPTION

Figure 1:
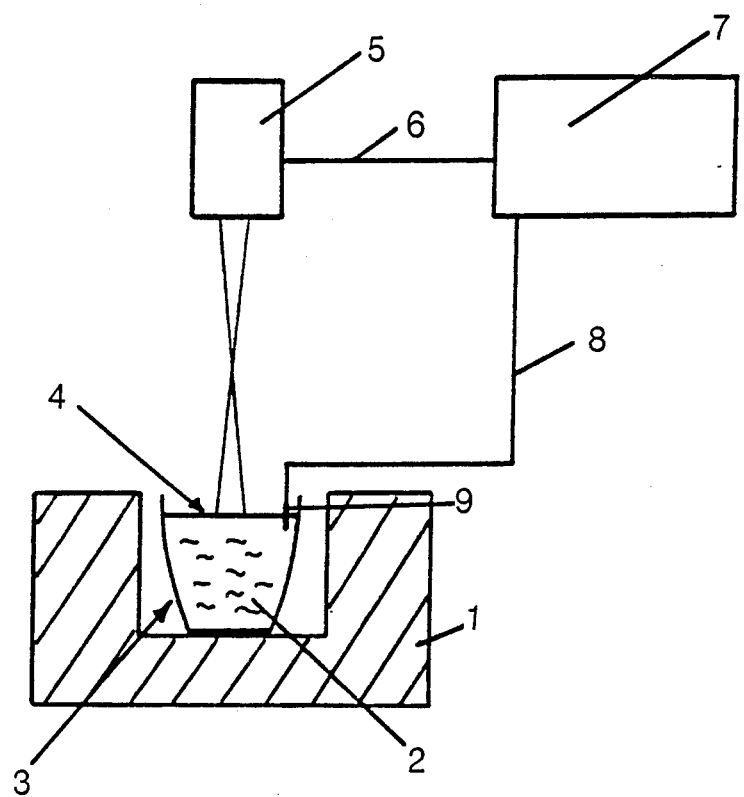
FIG. 1 is a schematic representation of a measuring device.

As shown in FIG. 1, a measuring device includes a furnace 1 with a power of for example 2 kW, the interior of which receives a crucible 3 filled with metal melt 2. An infra-red radiation pyrometer 5 with a band width of, for example, 2.8–3.3 $\mu$m is directed onto the melt surface 4, and is connected by a lead 6 to an indicating instrument 7. Connected with the indicating instrument 7, by a further lead 8, there is a thermo-element 9 for checking the surface temperature of the metal melt 2. Not shown in the drawing is a scraper, necessary for removal of the oxide skin, which is held always at the same temperature as the metal melt, so that the measuring results are not falsified by temperature variations during the removal of the oxide skin.

Figure 2:
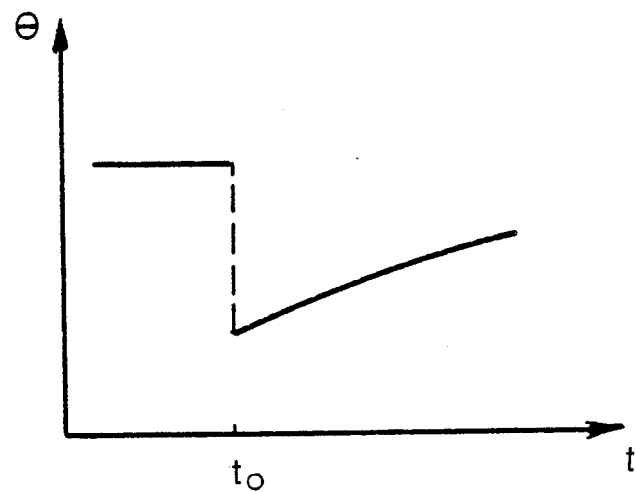
FIGS. 2a and 2b are graphic representations of measurement results.
Figure 2:
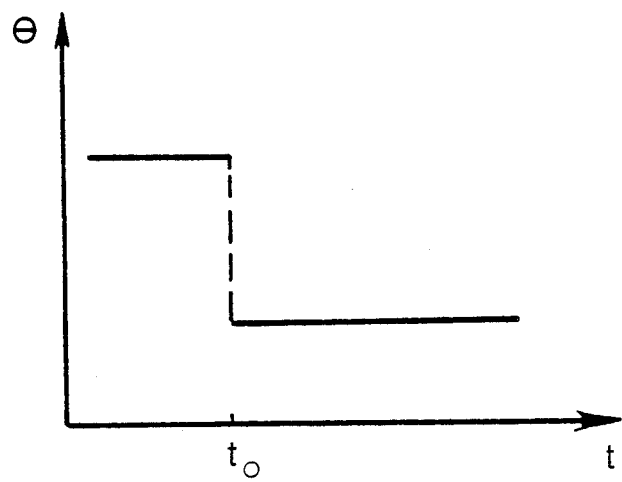

In FIG. 2 there are shown graphically the experimental results on aluminum melts with a lithium content of 3 ppm (2a) and <0.5 ppm (2b) respectively. With the presence of lithium in the metal melt, after the removal of the oxide skin from the melt surface at $t_o$, the electrical voltage $\theta$ measured at the pyrometer output at once rises rapidly, as a consequence of the rapid new formation of the oxide skin. If, on the other hand, practically no lithium is present in the melt, the oxide skin increases significantly more slowly, that is, the increase in the electrical voltage $\theta$ measured at the pyrometer output follows a corresponding flatter course after the removal of the oxide skin.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. A process for measuring the rate of oxidation of a metal melt comprising providing a metal melt having an oxide skin on the surface thereof, providing an infra-red radiation pyrometer for measuring the intensity of the thermal radiation emanating from the surface of the metal melt, removing the oxide skin from the surface of the metal melt at a constant temperature, measuring the decrease in intensity of the thermal radiation emanating from the surface of the metal melt as a function of time during subsequent oxidation at the surface of the metal melt and determining the rate of oxidation at the surface of the melt.

2. A process for measuring the concentration of oxidation influencing elements in a metal melt comprising providing a metal melt having an oxide skin on the surface thereof, providing an infra-red radiation pyrometer for measuring the intensity of the thermal radiation emanating from the surface of the metal melt, removing the oxide skin from the surface of the metal melt at a constant temperature, measuring the decrease in intensity of the thermal radiation emanating from the surface of the metal melt as a function of time during subsequent oxidation at the surface of the metal melt and determining the concentration of oxidation influencing elements.

* * * * *